US011833335B2

(12) United States Patent
Ikushima

(10) Patent No.: US 11,833,335 B2
(45) Date of Patent: Dec. 5, 2023

(54) LIQUID MATERIAL EJECTING APPARATUS

(71) Applicant: MUSASHI ENGINEERING, INC., Mitaka (JP)

(72) Inventor: Kazumasa Ikushima, Mitaka (JP)

(73) Assignee: MUSASHI ENGINEERING, INC., Mitaka (JP)

( * ) Notice: Subject to any disclaimer, the term of this patent is extended or adjusted under 35 U.S.C. 154(b) by 519 days.

(21) Appl. No.: 16/979,593

(22) PCT Filed: Mar. 15, 2019

(86) PCT No.: PCT/JP2019/010989
§ 371 (c)(1),
(2) Date: Sep. 10, 2020

(87) PCT Pub. No.: WO2019/181812
PCT Pub. Date: Sep. 26, 2019

(65) Prior Publication Data
US 2021/0001054 A1    Jan. 7, 2021

(30) Foreign Application Priority Data

Mar. 20, 2018  (JP) .................................. 2018-053474

(51) Int. Cl.
*B05C 11/10*        (2006.01)
*B05C 5/02*         (2006.01)
(Continued)

(52) U.S. Cl.
CPC .... *A61M 5/31576* (2013.01); *A61M 5/31513* (2013.01); *A61M 5/31528* (2013.01); *A61M 5/31548* (2013.01); *B05C 5/0225* (2013.01); *B05C 11/1031* (2013.01); *A61M 2005/3128* (2013.01); *B05C 5/0233* (2013.01); *B05D 1/26* (2013.01)

(58) Field of Classification Search
CPC . B05C 5/0225; B05C 11/1031; B05C 5/0233; B05D 1/26
See application file for complete search history.

(56) References Cited

U.S. PATENT DOCUMENTS 5,350,600 A * 9/1994 Kubota ................. B05C 5/0225
                                                  118/301
5,495,963 A * 3/1996 Miller ..................... F16K 47/04
                                                  251/126
(Continued)

FOREIGN PATENT DOCUMENTS

CN          85108663 A      6/1987
CN         106102933 A     11/2016
(Continued)

OTHER PUBLICATIONS

International Search Report dated May 7, 2019, issued in counterpart Application No. PCT/JP2019/010989. (2 pages).
(Continued)

*Primary Examiner* — Jeremy Carroll
(74) *Attorney, Agent, or Firm* — WHDA, LLP

(57) ABSTRACT

Problem: To provide a liquid-material discharge device that enables easier correction of a changed discharge amount during discharge operation than conventional techniques. Solution: A liquid-material discharge device according to the present invention, which includes a discharging member having a rod-shaped body, a liquid chamber wider than the discharging member, in which a tip portion of the discharging member is disposed, a discharge port communicating with the liquid chamber, a liquid feed path that makes the liquid chamber communicate with a liquid-material reservoir, and a driving device configured to drive the discharging member, includes a discharge amount adjustment member positioned at the liquid feed path, and a member position adjustment mechanism configured to shift a position of the discharge amount adjustment member within the liquid feed path, the discharge amount adjustment member being kept from interrupting communication between the liquid chamber and the liquid-material reservoir.

20 Claims, 11 Drawing Sheets

(51) Int. Cl.
  *B05D 1/26*    (2006.01)
  *A61M 5/315*   (2006.01)
  *A61M 5/31*    (2006.01)

(56) References Cited

U.S. PATENT DOCUMENTS

| | | | |
|---|---|---|---|
| 8,448,818 | B2 | 5/2013 | Ikushima |
| 8,807,400 | B2 | 8/2014 | Ikushima |
| 9,821,323 | B2 | 11/2017 | Kushima |
| 2006/0093493 | A1 | 5/2006 | Maruyama et al. |
| 2014/0217127 | A1* | 8/2014 | Ikushima ............. H05K 3/0091 222/420 |
| 2017/0006605 | A1 | 1/2017 | Seo et al. |

FOREIGN PATENT DOCUMENTS

| | | | | |
|---|---|---|---|---|
| EP | 1155748 | A1 * | 11/2001 | ......... B05C 11/1034 |
| JP | H05-317777 | A | 12/1993 | |
| JP | 2002-326715 | A | 11/2002 | |
| JP | 2002-361147 | A | 12/2002 | |
| JP | 2006-35149 | A | 2/2006 | |
| JP | 2013-107035 | A | 6/2013 | |
| WO | 2008/126373 | A1 | 10/2008 | |
| WO | 2013/111855 | A1 | 8/2013 | |

OTHER PUBLICATIONS

International Preliminary Report on Patentability (Form PCT/IPEA/409) issued in counterpart International Application No. PCT/JP2019/010989 dated Jul. 2, 2020, with English Translation. (7 pages).

Office Action dated Apr. 1, 2022, issued in counterpart IN application No. 202017044356, with English Translation. (6 pages).

Office Action dated Oct. 22, 2021, issued in counterpart CN application No. 201980020733.2, with English translation. (12 pages).

Extended (Supplementary) European Search Report dated Nov. 16, 2021, issued in counterpart EP application No. 19771922.2. (8 pages).

* cited by examiner

[Fig.1]
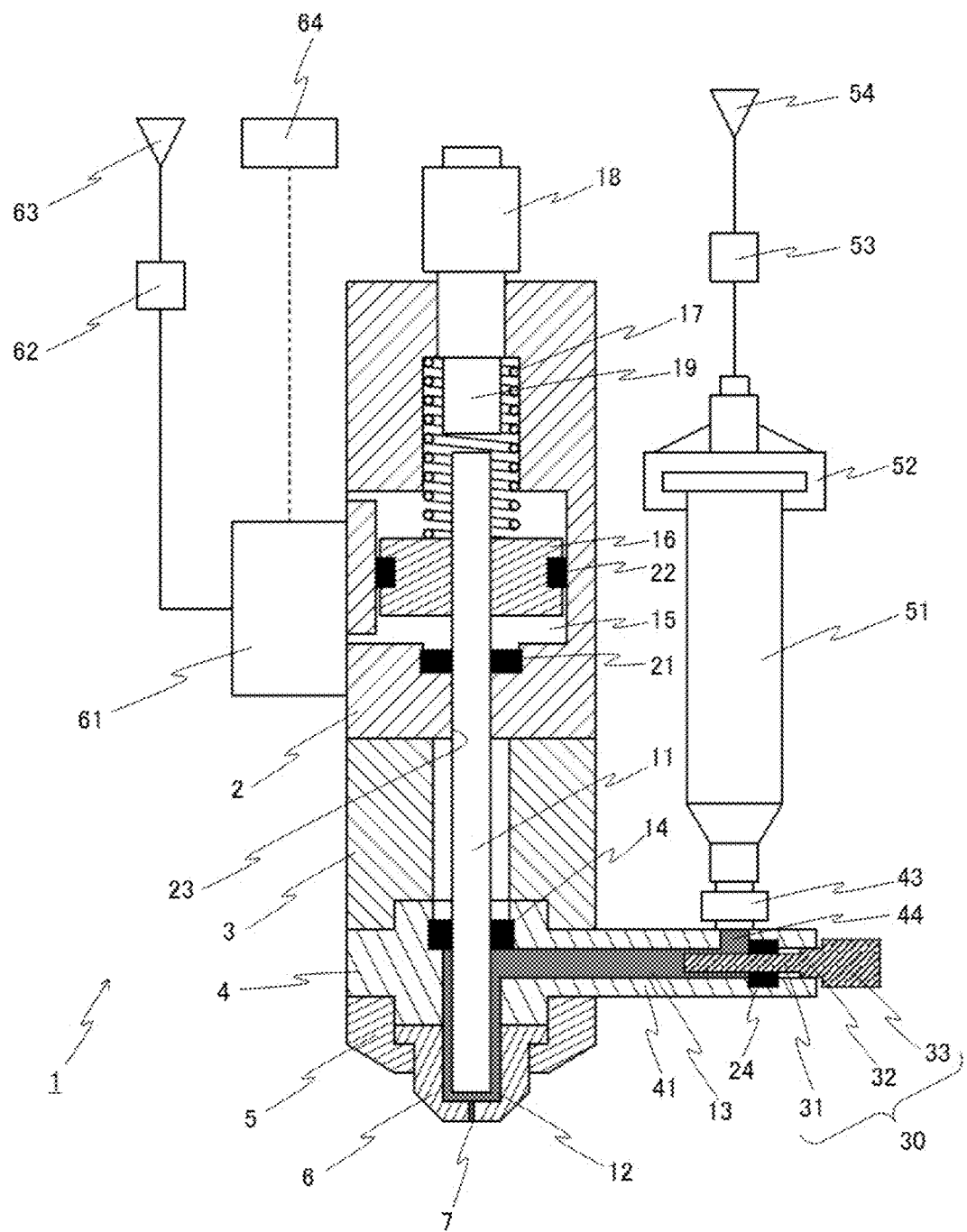

[Fig.2]
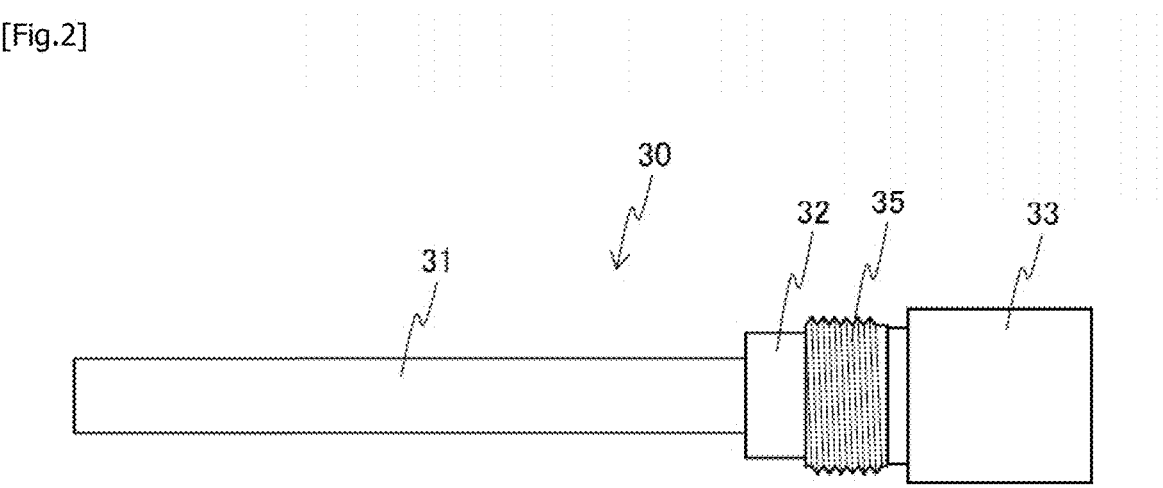
[Fig.3]
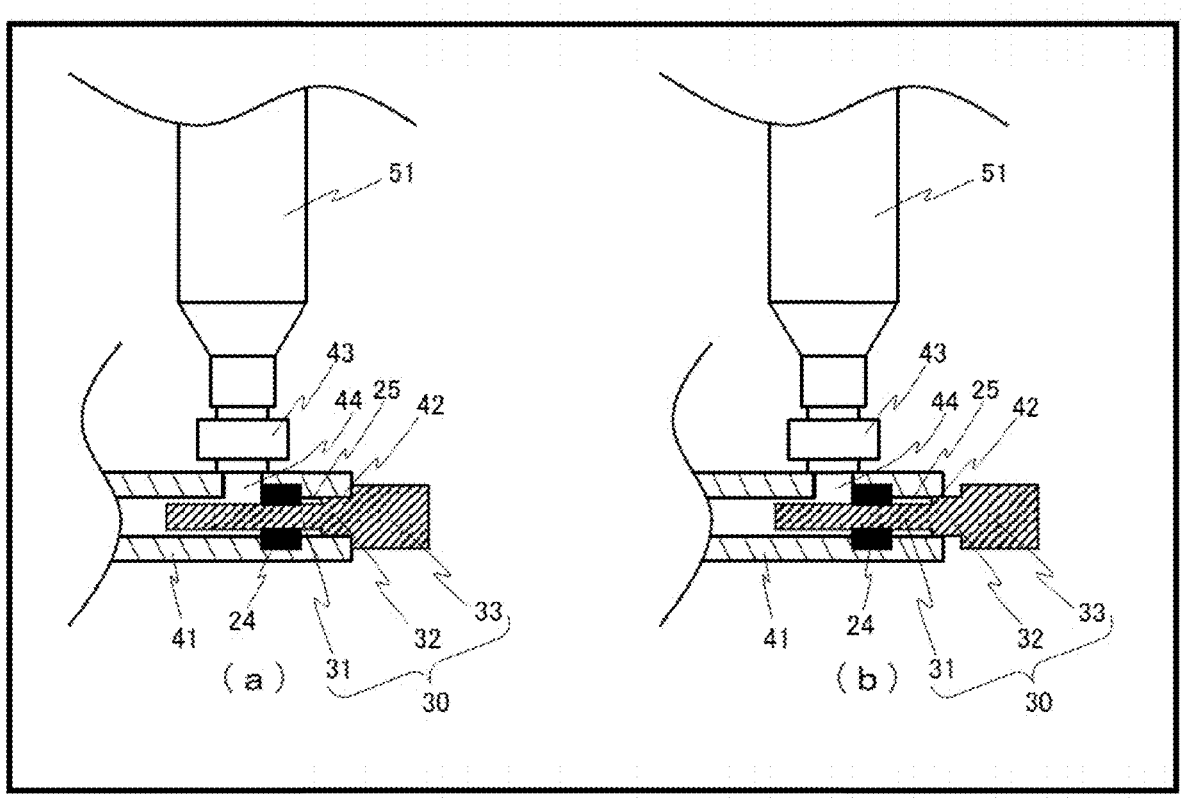

[Fig.4]
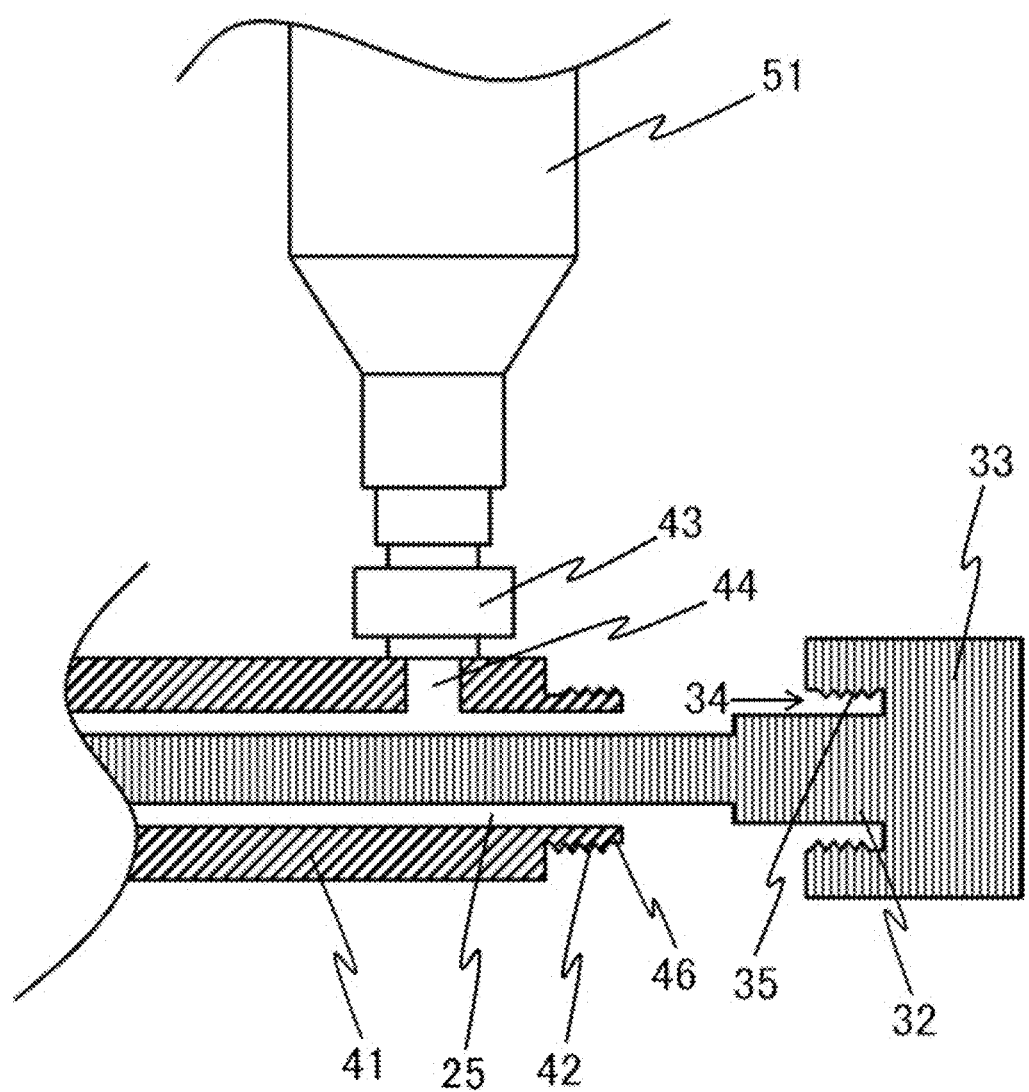

[Fig.5]
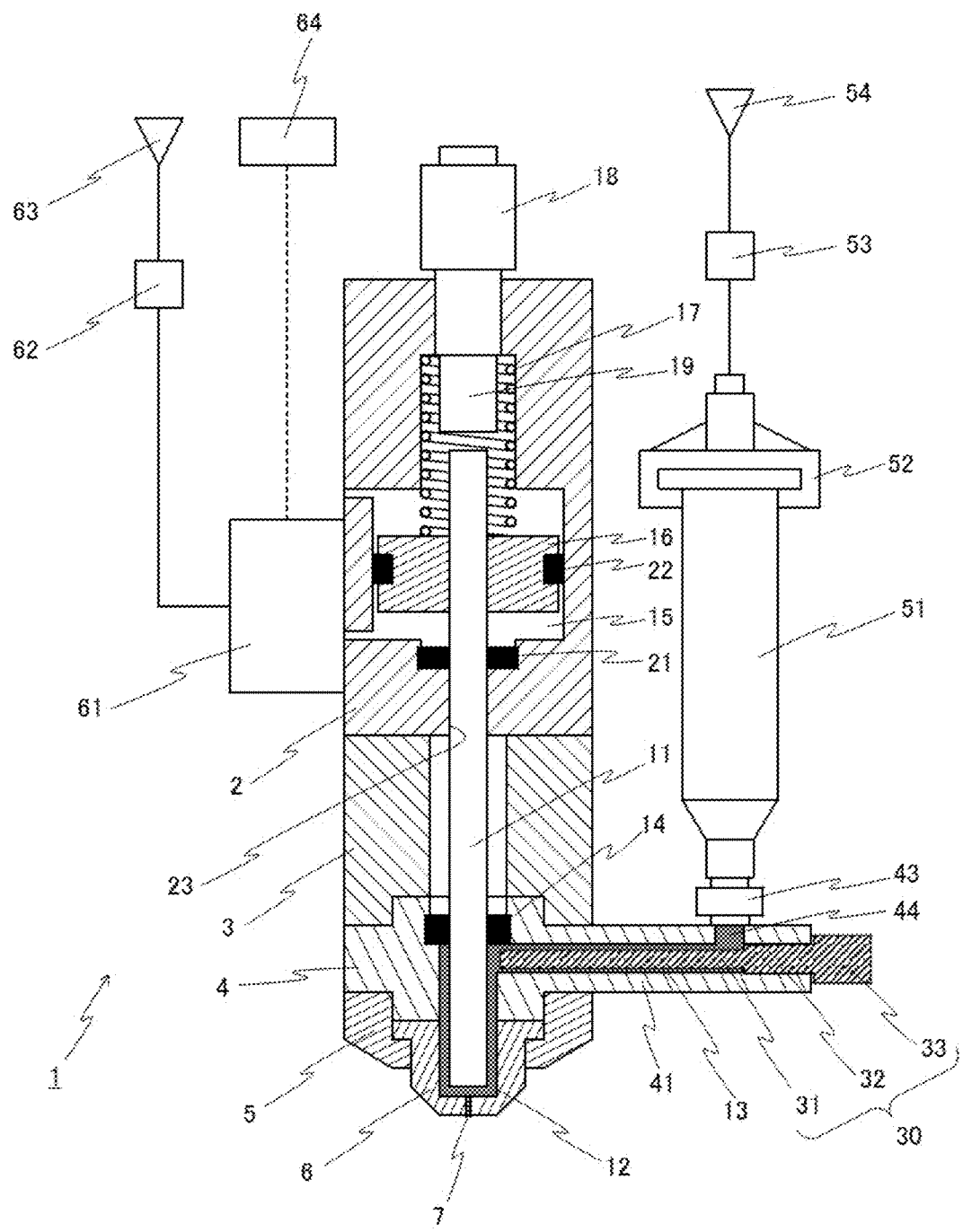

[Fig.6]
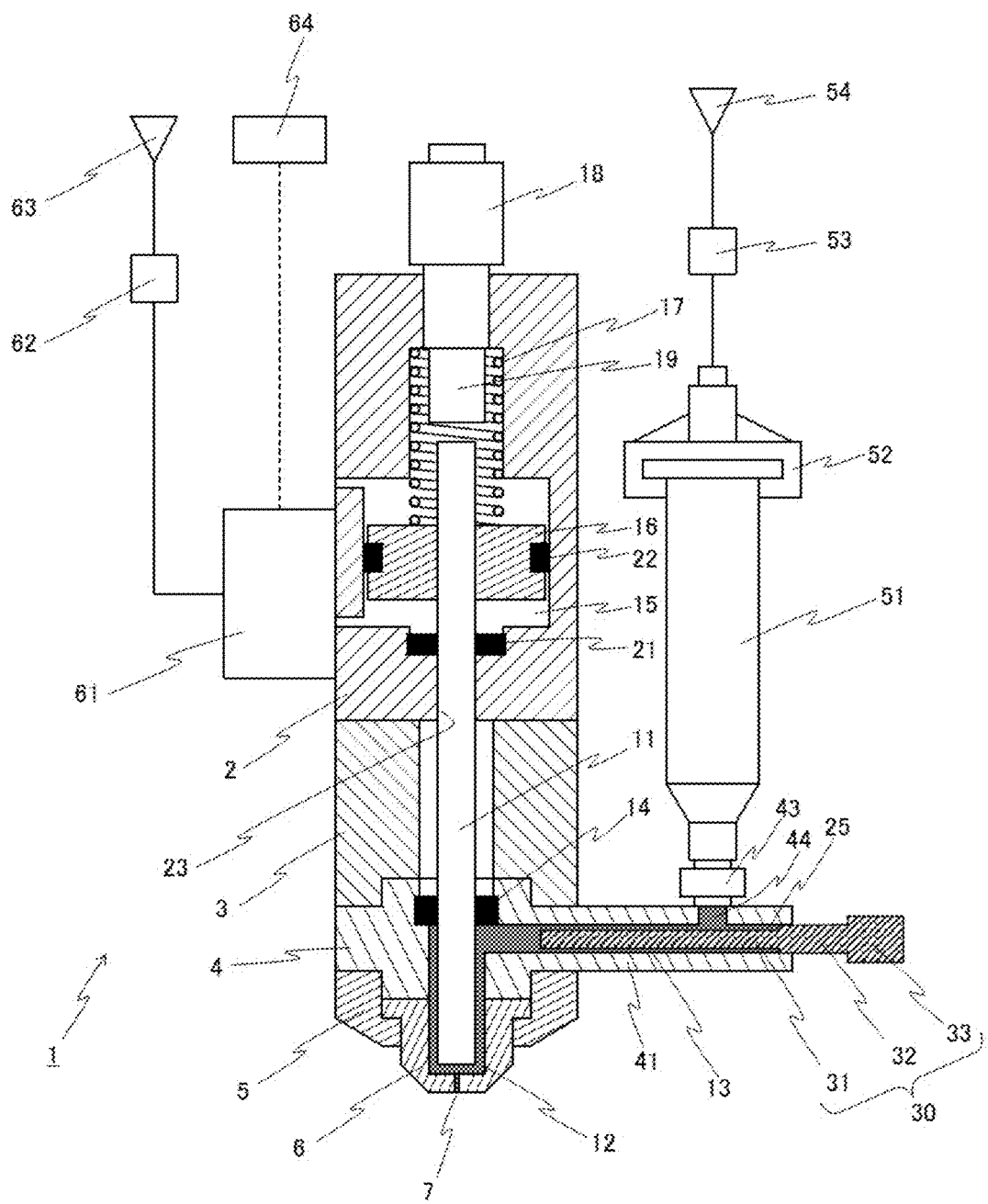

[Fig.7]
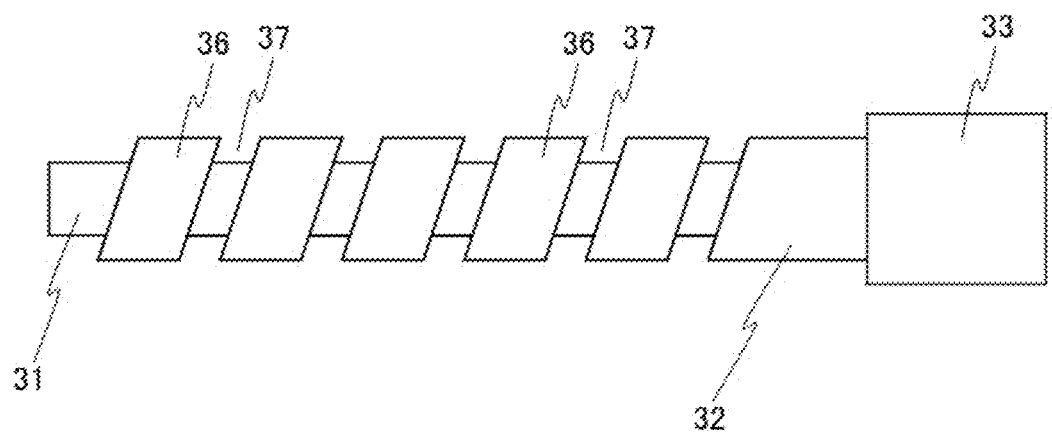

[Fig.8]
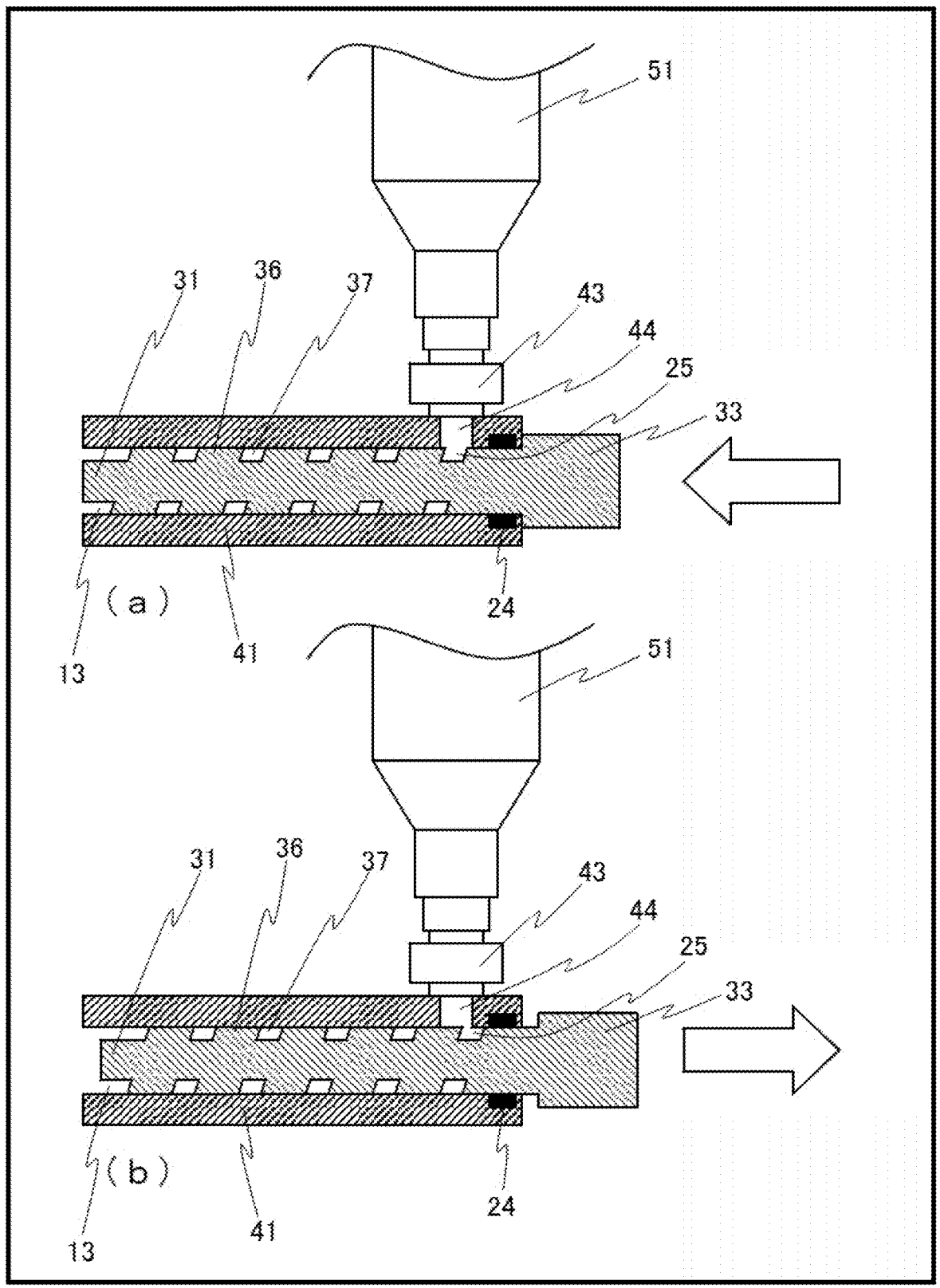

[Fig.9]
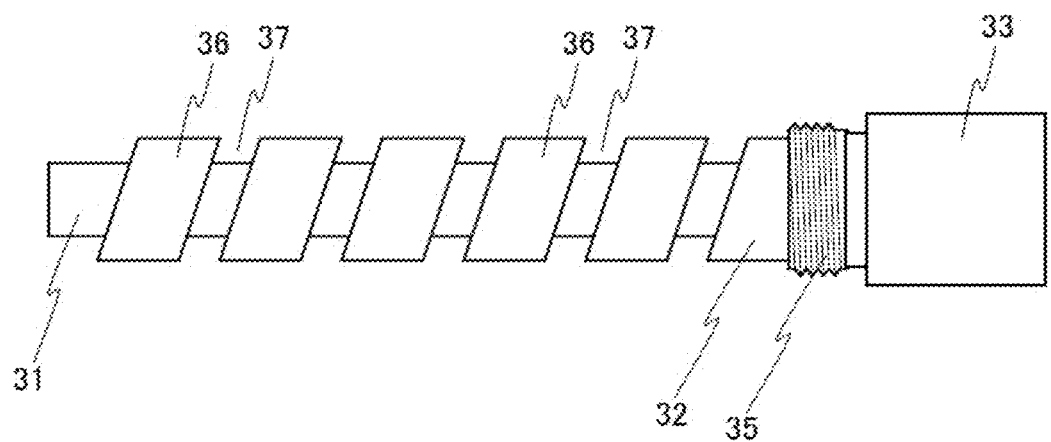

[Fig.10]
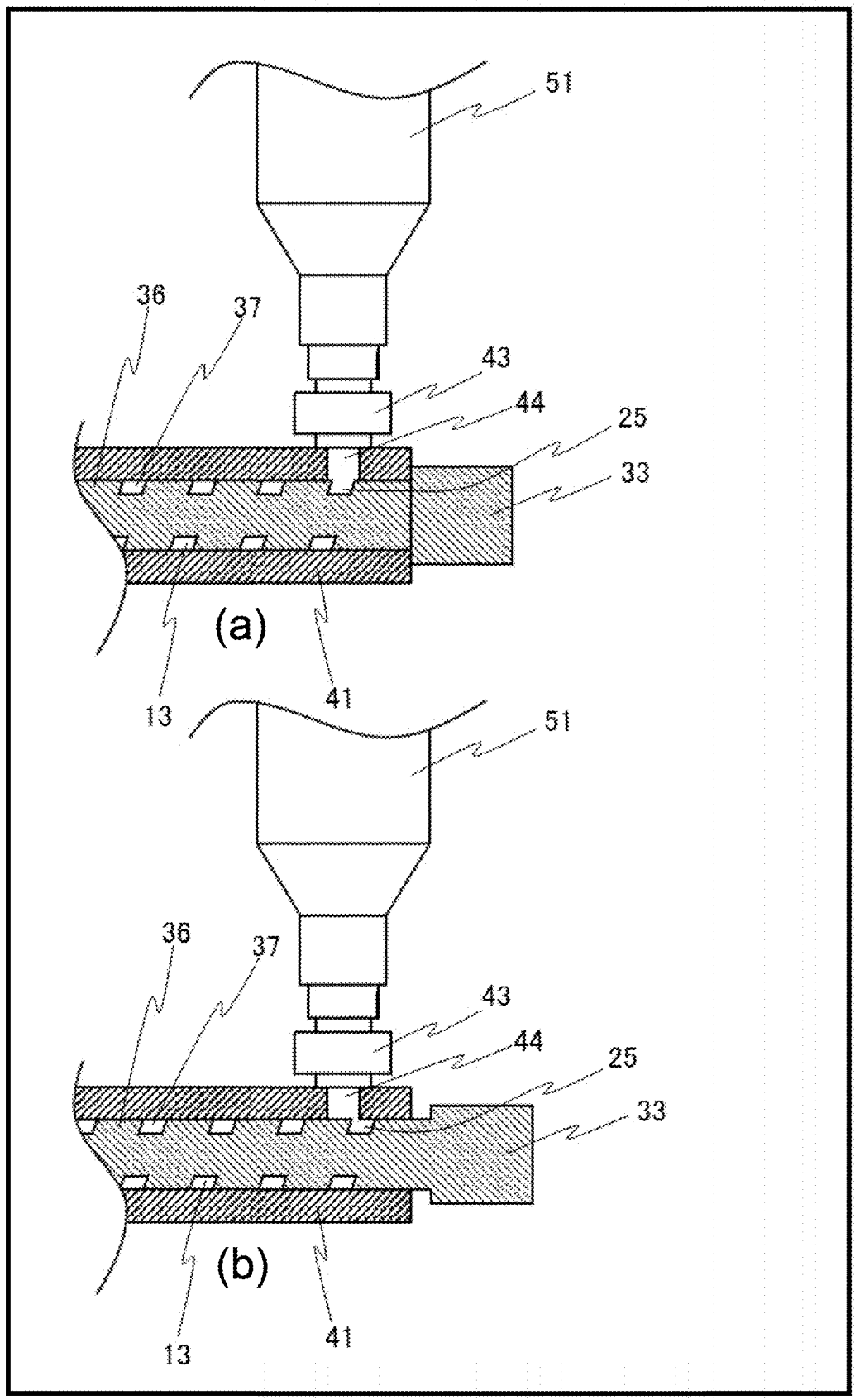

[Fig.11]
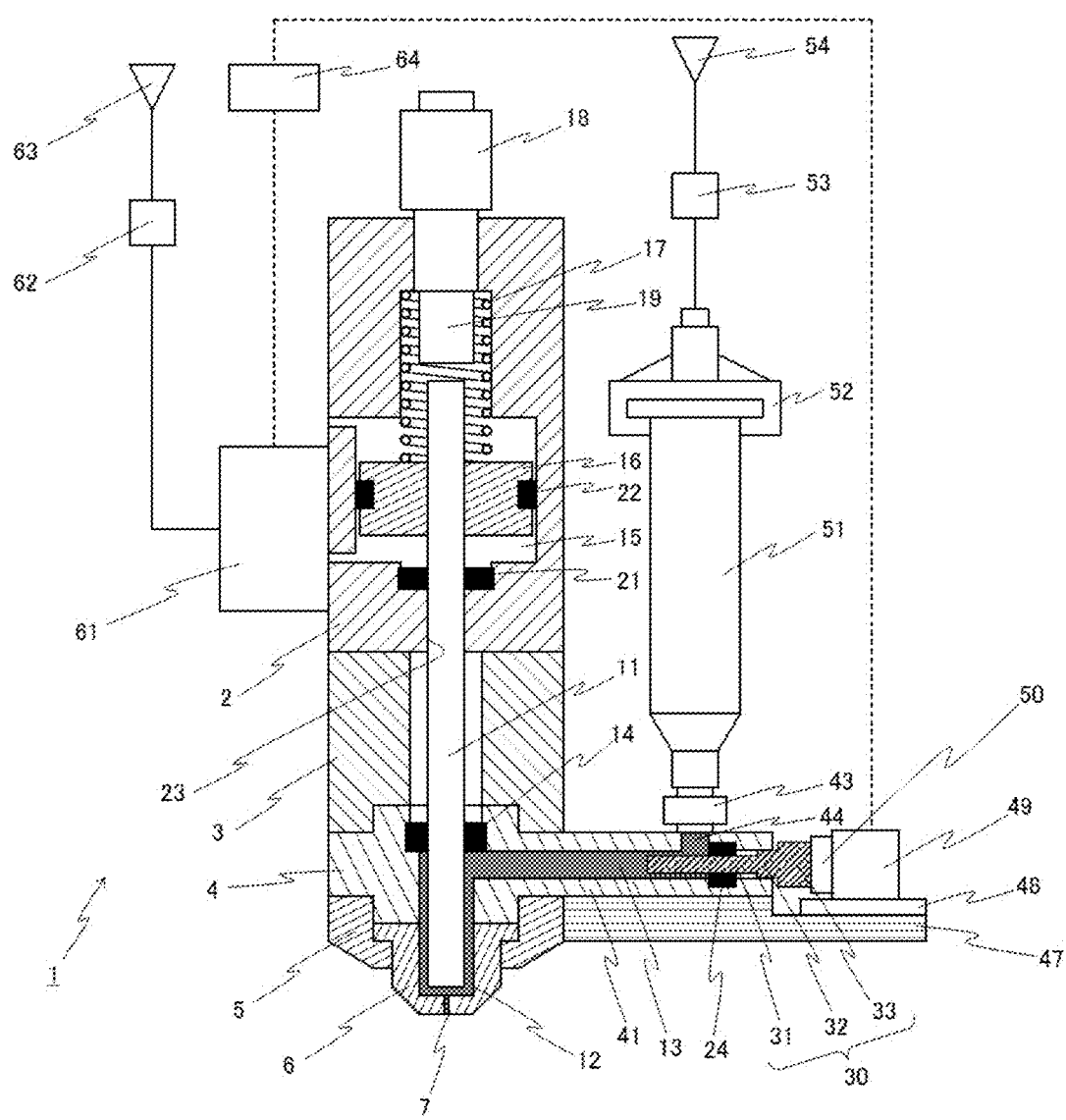

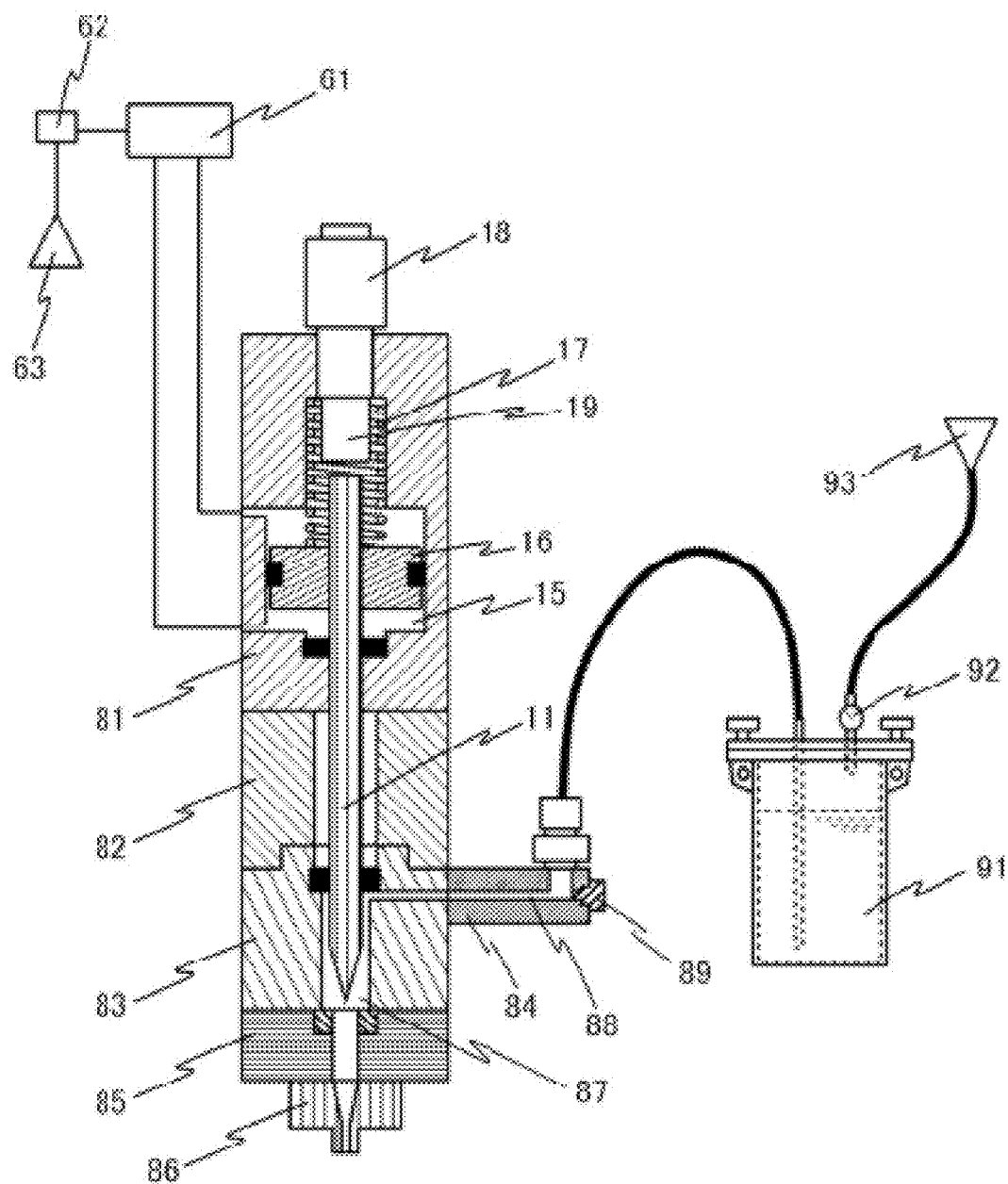
[Fig.12] RELATED ART

LIQUID MATERIAL EJECTING APPARATUS

TECHNICAL FIELD

The present invention relates to a liquid-material discharge device that enables easier correction of a changed discharge amount during discharge operation than conventional techniques.

BACKGROUND ART

As a discharge device for applying liquid material such as adhesive in a desired pattern onto a substrate, there are known a discharge device that discharges a small amount of liquid material from a discharge port by using a rod-shaped body (plunger) that reciprocates, and a discharge device that discharges liquid material by rotating a screw including a helical vane formed on a surface of a rod-shaped body in an axial direction and thereby causing the vane to carry the liquid material.

In Patent Document 1, for example, the applicant disclosed a discharge device including: a liquid chamber having a discharge port through which liquid material is discharged; an extrusion member having a plunger and a contact portion, the plunger being narrower than the liquid chamber and including a tip portion that moves forward and backward within the liquid chamber; a collision member disposed adjacent to the extrusion member at a side opposite to the plunger and having a piston and a collision portion facing the contact portion; and driving means that causes the extrusion member and the collision member to move forward and backward, where collision of the collision portion against the contact portion causes the extrusion member to advance at high speed and the liquid material to be discharged.

In Patent Document 2, for example, the applicant disclosed a liquid-material discharge device, which is a screw type discharge device that causes liquid material to be discharged by rotation of a screw, including: a screw having a helical blade formed on a cylinder surface in a longitudinal direction from a tip thereof; a motor that rotates the screw; a main body having a liquid-material inlet through which liquid material is supplied, a screw through-hole through which the screw passes, and a housing covering a tip of the screw at a discharge-port side; and a nozzle attached to a tip of the housing and communicating with the inside of the housing, where the liquid-material discharge device has a gap between the screw and an inner wall surface of the housing.

PRIOR ART LIST

Patent Document

Patent Document 1: International Publication No. 2008/126373 pamphlet
Patent Document 2: Japanese Patent Laid-Open Publication No. 2002-326715

SUMMARY OF THE INVENTION

Problems to be Solved by the Invention

Viscosity of a liquid material may change due to a change in surrounding conditions and a lapse of time, and a discharge amount thereof may change in some cases. In such cases, it is required to correct the discharge amount by adjusting an air pressure applied to a liquid reservoir. However, correcting the changed discharge amount needed effort and time such as a trial and error process for calculating an appropriate air pressure.

Thus, an object of the present invention is to provide a liquid-material discharge device that enables easier correction of a changed discharge amount during discharge operation than conventional techniques.

Means for Solving the Problems

A liquid-material discharge device according to the present invention, which includes a discharging member having a rod-shaped body, a liquid chamber wider than the discharging member, in which a tip portion of the discharging member is disposed, a discharge port communicating with the liquid chamber, a liquid feed path that makes the liquid chamber communicate with a liquid-material reservoir, and a driving device configured to drive the discharging member, includes a discharge amount adjustment member positioned at the liquid feed path, and a member position adjustment mechanism configured to shift a position of the discharge amount adjustment member within the liquid feed path, the discharge amount adjustment member being kept from interrupting communication between the liquid chamber and the liquid-material reservoir.

In the liquid-material discharge device, the liquid feed path may include a linear flow path having an end opening, and the discharge amount adjustment member may be constituted by an elongated member inserted in the liquid feed path.

The liquid-material discharge device may include a seal member through which the discharge amount adjustment member is inserted.

In the liquid-material discharge device, the discharge amount adjustment member may have a length of one-half to one times a length L of the liquid feed path.

In the liquid-material discharge device, a tip portion of the discharge amount adjustment member may be positioned at a liquid-chamber side from an inlet via which the liquid-material reservoir is connected to the liquid feed path.

In the liquid-material discharge device, the member position adjustment mechanism may be constituted by a first thread groove formed on a liquid feed member in which the liquid feed path is formed, and a second thread groove formed on the discharge amount adjustment member corresponding to the first thread groove.

In the liquid-material discharge device, the member position adjustment mechanism may be constituted by a forward and backward driving device configured to drive the discharge amount adjustment member forward and backward.

The liquid-material discharge device may include a control device configured to control positioning of the discharge amount adjustment member by the forward and backward driving device at a preset timing.

In the liquid-material discharge device, the discharge amount adjustment member may be removably inserted into the liquid feed path.

In the liquid-material discharge device, the discharge amount adjustment member may have a recessed and projected portion formed on a longitudinal surface.

In the liquid-material discharge device, the recessed and projected portion may be constituted by a ridge in contact with an inner periphery of the liquid feed path and a groove positioned between sections of the ridge.

In the liquid-material discharge device, the groove positioned between sections of the ridge may be a helical groove.

In the liquid-material discharge device, the discharge amount adjustment member may be selected out of a plurality of discharge amount adjustment members different in one or more of a cross-sectional area, a cross-sectional shape, and a length, and the selected discharge amount adjustment member may be able to be removably inserted into the liquid feed path.

In the liquid-material discharge device, the discharging member may be constituted by a plunger of which tip portion moves forward and backward within the liquid chamber, or a screw of which tip portion rotates within the liquid chamber.

In the liquid-material discharge device, the discharging member may be a plunger extending vertically, the driving device may be configured to move the discharging member forward and backward, and the plunger may be moved forward to collide against a valve seat provided on an inner bottom surface of the liquid chamber, or may be moved forward and stopped immediately before colliding against the valve seat, so that a liquid droplet is discharged and flied from the discharge port.

A liquid-material discharge method according to the present invention uses the liquid-material discharge device described above.

Advantageous Effect of the Invention

According to the present invention, it is possible to provide a liquid-material discharge device that enables easier correction of a changed discharge amount during discharge operation than conventional techniques.

BRIEF DESCRIPTION OF THE DRAWINGS

FIG. 1 is a front sectional view of a liquid-material discharge device according to a first embodiment.

FIG. 2 is a lateral view of a discharge amount adjustment member according to the first embodiment.

FIG. 3 is a front sectional view for describing a discharge amount adjustment method according to the first embodiment. (a) shows a state where the discharge amount adjustment member is set at a forwardmost position, and (b) shows a state where the discharge amount adjustment member has been moved backward from the forwardmost position.

FIG. 4 is a partial front sectional view of a liquid-material discharge device according to a second embodiment.

FIG. 5 is a front sectional view of a liquid-material discharge device (when a discharge amount adjustment member is moved forward) according to a third embodiment.

FIG. 6 is a front sectional view of the liquid-material discharge device (when the discharge amount adjustment member has been moved backward) according to the third embodiment.

FIG. 7 is a lateral view of a discharge amount adjustment member according to a fourth embodiment.

FIG. 8 is a front sectional view for describing a discharge amount adjustment method according to the fourth embodiment. (a) shows a state where the discharge amount adjustment member is set at a forwardmost position, and (b) shows a state where the discharge amount adjustment member has been moved backward from the forwardmost position.

FIG. 9 is a lateral view of a discharge amount adjustment member according to a fifth embodiment.

FIG. 10 is a front sectional view for describing a discharge amount adjustment method according to the fifth embodiment. (a) shows a state where the discharge amount adjustment member is set at a forwardmost position, and (b) shows a state where the discharge amount adjustment member has been moved backward from the forwardmost position.

FIG. 11 is a front sectional view of a liquid-material discharge device according to a sixth embodiment.

FIG. 12 is a front sectional view of a conventional liquid-material discharge device.

MODE FOR CARRYING OUT THE INVENTION

Conventional Example

A conventional liquid-material discharge device shown in FIG. 12 mainly includes an upper main body 81, a middle main body 82, a first liquid feed member 83, a second liquid feed member 84, a lower main body 85, and a nozzle member 86.

The upper main body 81 has a piston chamber 15 in which a piston 16 coupled to a rear portion of a discharging member 11 is vertically slidably disposed. The piston chamber 15 is supplied with pressurized air from an air supply source 63 via a solenoid switching valve 61 and a pressure regulator 62.

The discharging member 11 is a tapered rod-shaped body, and its tip portion is positioned in a liquid chamber 87 formed in the first liquid feed member 83, the lower main body 85, and the nozzle member 86. The discharging member 11 reciprocates by action of the pressurized air from the air supply source 63 and a spring 17, causing liquid material to be discharged from a discharge port formed at a lower end of the nozzle member 85.

The liquid chamber 87 communicates with a liquid feed path 88 via an opening provided in an upper lateral surface of the liquid chamber 87.

The liquid feed path 88 has, at an end portion opposite to the liquid chamber 87, a lateral opening into which a plug 89 is screwed. The liquid feed path 88 is filled with liquid material after the plug 89 is removed so that air bubbles are purged.

The liquid feed path 88 communicates with a storage tank 91 via a pipe. The storage tank 91 has an upper space to which pressurized air is supplied from an air supply source 93. The pressure of the air is regulated by a pressure reducing valve 92.

The conventional liquid-material discharge device has a problem that the liquid feed path 88 is too thin for general cotton swabs for industrial use to be inserted therein, which makes it difficult to remove the liquid material remaining in the liquid feed path.

First Embodiment

A liquid-material discharge device 1 according to a first embodiment of the present invention shown in FIG. 1 mainly includes an upper main body 2, a lower main body 3, a liquid feed member 4, a nozzle fixture 5, a nozzle member 6, and a controller 64.

The upper main body 2 is a block-like member having a rectangular parallelepiped shape, and has a piston chamber 15 inside. In the piston chamber 15, a piston 16 coupled to a rear portion of a discharging member 11 is vertically slidably disposed. The piston 16 is provided with an annular seal member 22 around a lateral surface, which maintains airtightness between an upper space and a lower space of the piston chamber 15. The piston chamber 15 has, in a bottom surface thereof, a depressed portion into which an annular seal member 21 is fitted. The piston chamber 15 has, at a center of the depressed portion in the bottom surface, a through-hole 23 extending vertically. The discharging member 11 is inserted through the seal member 21 and the through-hole 23.

The lower space of the piston chamber 15 is supplied with pressurized air through a solenoid switching valve 61. The solenoid switching valve 61 communicates with an air supply source 63 that supplies pressurized air, via a pressure regulator 62. The pressure regulator 62 is constituted by, for example, a pressure reducing valve or a combination of a pressure reducing valve and a buffer tank. In accordance with instructions from the controller 64, the solenoid switching valve 61 operates to switch between a first position that makes the pressure regulator 62 communicate with the lower space of the piston chamber 15, and a second position that makes the lower space of the piston chamber 15 communicate with the outside (atmosphere). When the solenoid switching valve 61 switches to the first position, the discharging member 11 is moved backward by action of the pressurized air, and when it switches to the second position, the discharging member 11 is moved forward by biasing force of a spring 17. That is, the solenoid switching valve 61 and the spring 17 constitute a driving device that drives the discharging member 11.

The controller 64 is a computer that controls the operation of the solenoid switching valve 61, and is connected to an input device not shown and a display device not shown.

In the present embodiment, the solenoid switching valve 61 is directly fixed to the upper main body 2. However, it may be positioned away from the upper main body 2 with a tube (pressure feed tube) or the like interposed therebetween.

The discharging member 11 is a valve element having a columnar shape, and extends vertically to pass through the upper main body 2, the lower main body 3, and the liquid feed member 4. A lower end portion of the discharging member 11 is positioned in a liquid chamber 12. When the discharging member 11 is separated from a valve seat provided on an inner bottom surface of the liquid chamber 12, a discharge port 7 communicates with the liquid chamber 12 and the liquid material is discharged. When the discharging member 11 is seated on the valve seat, the communication between the discharge port 7 and the liquid chamber 12 is interrupted and the discharge is stopped. The discharging member 11 is smaller in diameter than the liquid chamber 12, which keeps a lateral periphery of the discharging member 11 away from an inside surface of the liquid chamber 12. Friction generated on the lateral periphery of the discharging member 11 is thus minimized, which allows the discharging member 11 to move at high speed.

It should be noted that, unlike the discharge device 1 of the present embodiment, it is of course possible to apply the technical idea of the present invention to a jet-type discharge device that discharges liquid material to fly it from a discharge port by rapidly moving a valve element (discharging member) close to a valve seat or colliding it against the valve seat and thereby applying inertial force to the liquid material. The jet-type discharge device also uses the discharging member having a tip portion narrower than the liquid chamber so that the discharging member moves forward and backward at high speed.

Though the discharging member 11 has a flat end in FIG. 1, this is not a limitation. For example, it may be spherical, depressed, tapered, or projected at a position facing the discharge port 7. The discharging member 11 is not limited to the columnar valve element. For example, it may be constituted by a screw that rotates. The discharging member to which the present invention is applied may be a rod-shaped member extending in a vertical direction, which reciprocally moves forward and backward or rotates so that the liquid material in the liquid chamber is discharged from the discharge port. The driving device that drives the discharging member is, for example, a motor, a piezoelectric element, an elastic body such as a spring and a pressurized-air switching valve, or a pneumatic actuator.

The piston 16 is coupled to the rear portion of the discharging member 11, and is biased downward by the spring 17. The spring 17 is a coil spring. In an internal space of the spring 17, a rear end portion of the discharging member 11 and a stroke adjustment screw 19 are arranged opposite to each other. The stroke adjustment screw 19 is coupled to a knob 18 inserted into the upper main body 2 from its upper surface. Turning the knob 18 allows for adjusting a backwardmost position of the discharging member 11.

The lower main body 3 that is a block-like member having a rectangular parallelepiped shape is disposed under the upper main body 2. The lower main body 3 has a vertical through-hole larger in diameter than the discharging member 11, through which the discharging member 11 is inserted. The liquid feed member 4 longer in a horizontal direction than the lower main body 3 is disposed under the lower main body 3. The nozzle fixture 5 is disposed under the liquid feed member 4. The nozzle fixture 5 has a bowl shape provided with an opening in a bottom surface thereof, and holds a flange portion of the nozzle member 6 inserted in the opening to couple the liquid feed member 4 to the nozzle member 6. The liquid feed member 4 and the nozzle member 6 can be easily removed from the lower main body 3 and the nozzle fixture 5.

The liquid feed member 4 has a stepped through-hole extending vertically. The stepped portion of the stepped through-hole is provided with an annular seal member 14, and a space of the stepped through-hole below the seal member 14 constitutes a part of the liquid chamber 12. Since a width (diameter) of the liquid chamber 12 is greater than that of the discharging member 11, the lateral periphery of the discharging member 11 is kept away from the inside surface of the liquid chamber 12. The seal member 14 has a hole substantially equal in diameter to the discharging member 11, through which the discharging member 11 is inserted.

The liquid feed member 4 includes an extension portion 41 straightly extending in the horizontal direction from an extension beyond lateral surfaces of the main bodies (2, 3). The extension portion 41 has the liquid feed path 13 straightly extending in the horizontal direction inside. The liquid feed path 13 has a constant diameter over an entire length of a section from an inlet 44 to the liquid chamber 12. An end portion of the liquid feed path 13 at a side opposite to the liquid chamber 12 is provided with an annular seal member 24 through which a discharge amount adjustment member 30 is inserted. The extension portion 41 has such a length that a reservoir 51 can be easily replaced. As in the conventional example shown in FIG. 12, the extension portion 41 may be constituted detachably at the extension of the lateral surfaces of the main bodies (2, 3) (that is, the extension portion 41 may be constituted by the second liquid feed member 84 in FIG. 12).

The liquid feed member 4 has a height (width in the vertical direction) smaller than those of the upper main body 2 and the lower main body 3. The liquid feed member 4 in the present embodiment is compact (thin) in the vertical direction, and thus suited to be cleaned by an ultrasonic cleaner.

It should be noted that, unlike the present embodiment, it is also possible to use a liquid feed member in which a liquid feed path extends straightly in an oblique direction (though, the width in the vertical direction becomes larger).

The liquid chamber 12 communicates with the liquid feed path 13 via an opening provided in an upper lateral surface of the liquid chamber 12. The liquid feed path 13 preferably has such a diameter that a cotton swab for industrial use can be inserted thereinto. The diameter is, for example, 2.5 mm to 10 mm (preferably 3 mm or more, or more preferably 4 mm or more). General cotton swabs for industrial use often have a head with a diameter of about 5 mm.

The inlet 44 is an opening provided in an upper surface of the liquid feed path 13 near the end portion at the side opposite to the liquid chamber 12, and communicates with the reservoir 51. The liquid material in the reservoir 51 is supplied to the liquid feed path 13 via the inlet 44.

The reservoir 51 is a commercial syringe made of resin or metal, and is detachably attached to the liquid feed member 4 with a reservoir coupler 43. The reservoir coupler 43 couples a lower end portion of the reservoir 51 to the extension portion 41 of the liquid feed member 4, and places the reservoir 51 in a position lateral to the main bodies (2, 3). The reservoir 51 has an upper opening to which an adapter 52 communicating with a pressure reducing valve 53 via a tube is attached. The reservoir 51 has an upper space to which pressurized air is supplied from an air supply source 54, the pressure of the air being regulated by the pressure reducing valve 53.

It should be noted that, unlike the present embodiment, a part of the flow path via which the reservoir 51 and the liquid chamber 12 communicate with each other may be constituted by a flexible tube of which flow-path cross-sectional area is changed by an operation of a clamping mechanism that clamps this tube from outside. The larger an amount by which the clamping mechanism compresses the tube, the smaller the cross-sectional area of the tube and the less an amount of liquid material being supplied. In this case, the tube may be clamped from both sides of the outside surface, or may be arranged in contact with a wall at one side of the outside surface and pressed against the wall from the other opposite side thereof.

The liquid feed path 13 has, at the end portion opposite to the liquid chamber 12, a lateral opening 45 through which the discharge amount adjustment member 30 is inserted. The liquid feed path 13 near the lateral opening 45 communicates with an insertion hole 25 having a first thread groove 42 formed in its inner periphery. In the first embodiment, a member position adjustment mechanism is constituted by the first thread groove 42 formed in the insertion hole 25 communicating with the liquid feed path 13 and a below-mentioned second thread groove 35 formed in an outer periphery of a plug portion 32 of the discharge amount adjustment member 30. The seal member 24 is removably disposed at the end portion of the liquid feed path 13 at the side opposite to the liquid chamber 12.

The discharge amount adjustment member 30 includes a stick-shaped insert portion 31, a plug portion 32 provided at an end portion of the insert portion 31, and a large-diameter portion 33 continuous with the insert portion 31 and the plug portion 32. The discharge amount adjustment member 30 serves to adjust resistance (in-tube resistance, flow resistance) in the flow path via which the reservoir 51 and the liquid chamber 12 communicate with each other.

The insert portion 31 is a columnar member smaller in diameter than the liquid feed path 13, and has such a length that its tip portion reaches at least the inlet 44 or, more preferably, is positioned at a liquid-chamber 12 side from the inlet 44. The reason is that moving the insert portion 31 having such a length forward and backward enables easy adjustment of the flow resistance in the liquid feed path 13. From a viewpoint of reducing an amount of liquid material remaining in the liquid feed path 13 when the insert portion 31 has been removed, the insert portion 31 preferably has, for example, a length of one-half to one times or, more preferably, two-thirds to one times a length L of the liquid feed path 13. In order to prevent damage to the inner periphery of the liquid feed path 13 while the insert portion 31 is inserted and removed, at least a surface of the insert portion 31 is preferably made of material softer than the inner periphery of the liquid feed path 13. It is disclosed that, for example, when the inner periphery of the liquid feed path 13 is made of metal, the surface (or the entire body) of the insert portion 31 is made of rubber or resin.

In the first embodiment, the liquid feed path 13 has a diameter of 3 mm, and the insert portion 31 has a diameter of 2 mm. Further, in the first embodiment, the insert portion 31 has a cross-sectional shape similar to a cross-sectional shape of the liquid feed path 13. The insert portion 31 is inserted into the liquid feed path 13 and the large-diameter portion 33 is manually turned for screwing, which causes the insert portion 31 to be fixed with its position on a center axis of the liquid feed path 13.

Since the amount of liquid material remaining in the liquid feed path 13 can be reduced by inserting the stick-shaped insert portion 31 into the liquid feed path 13 and thereby reducing a volume of the liquid feed path 13, it is possible to reduce an amount of liquid material wasted in cleaning of the liquid feed member 4. It is also possible to adjust an amount of liquid material supplied through the liquid feed path 13 to the liquid chamber 12 depending on intended usage by preparing a plurality of discharge amount adjustment members 30 each having an insert portion 31 different in cross-sectional area. It is disclosed that, for example, the discharge amount adjustment member 30 used for a liquid material having high viscosity has an insert portion 31 smaller in cross-sectional area than that of the discharge amount adjustment member 30 used for a liquid material having low viscosity. Herein, the discharge amount adjustment member 30 as a replacement candidate only has to enable adjustment of the amount of liquid material supplied through the liquid feed path 13 to the liquid chamber by replacement, and is not limited to the illustrated one having the insert portion 31 different in cross-sectional area. A similar effect can also be achieved by preparing a plurality of discharge amount adjustment members 30 each having an insert portion 31 different in one or more of a cross-sectional area, a cross-sectional shape, and a length.

The plug portion 32 is a columnar portion larger in diameter than the insert portion 31, and has a second thread groove 35 in its surface that is screwed into the first thread groove 42. Alternatively, the plug portion 32 may not have a second thread groove 35. The discharge amount adjustment member 30 may be fixed to the liquid feed member 4 by a positioning member that positions the discharge amount adjustment member 30 within the liquid feed path 13.

The large-diameter portion 33 is a columnar portion larger in diameter than the plug portion 32, and has a surface on which non-slip treatment has been applied. When the discharge amount adjustment member 30 is inserted into the lateral opening 45 provided in a lateral surface of the liquid feed member 4, manually pinching and turning the large-diameter portion 33 in a first direction (clockwise direction) causes the discharge amount adjustment member 30 to move forward in the liquid feed path 13, and turning it in a second direction (anticlockwise direction) causes the discharge amount adjustment member 30 to move backward in the liquid feed path 13. The second thread groove 35 of the plug portion 32 and the first thread groove 42 are tightly fitted together by screwing, and the position of the discharge amount adjustment member 30, which has been adjusted by turning the large-diameter portion 33, remains fixed even when the hold on the large-diameter portion 33 is released. Alternatively, the large-diameter portion 33 may be coupled to a rotation driving device such as a motor, of which rotation number can be controlled automatically by the controller 64 (see also a below-mentioned sixth embodiment).

FIG. 2 is a lateral view of a discharge amount adjustment member 30. Liquid material not shown adheres to a surface (periphery) of the insert portion 31 that has been drawn out. In order to reduce the amount of liquid material remaining in the liquid feed path 13 when the insert portion 31 is removed, the insert portion 31 may have, on the surface thereof, recesses and projections, or an annular ridge for scraping out the liquid material (see a below-mentioned fourth embodiment also).

FIG. 3 is a front sectional view illustrating a discharge amount adjustment method according to the first embodiment. (a) shows a state where the discharge amount adjustment member 30 is set at a forwardmost position, and (b) shows a state where the discharge amount adjustment member 30 has been moved backward from the forwardmost position. The flow resistance in the liquid feed path 13 is highest when the discharge amount adjustment member 30 is set at the forwardmost position. Conversely, the flow resistance in the liquid feed path 13 becomes lower as the discharge amount adjustment member 30 is moved backward from the forwardmost position. In the liquid-material discharge device that discharges liquid material by a pressure of pressurized air applied to the reservoir 51 like the first embodiment, as the flow resistance in the liquid feed path 13 becomes lower, the liquid material more easily flows from the reservoir 51 to the liquid chamber 12, resulting in an increase in the discharge amount. Conversely, as the flow resistance in the liquid feed path 13 becomes higher, the liquid material less easily flows from the reservoir 51 to the liquid chamber 12, resulting in a decrease in the discharge amount. Accordingly, for example, when a change over time causes higher viscosity of the liquid material and a decrease in the discharge amount, the discharge amount can be corrected into an appropriate amount by adjusting an amount of backward movement of the discharge amount adjustment member 30. For example, when an ambient temperature change causes lower viscosity of the liquid material and an increase in the discharge amount, the discharge amount can be corrected into an appropriate amount by adjusting an amount of forward movement of the discharge amount adjustment member 30.

In the above-mentioned jet-type discharge device, forward movement of the discharge amount adjustment member may result in an increase in the discharge amount, and the backward movement thereof may result in a decrease in the discharge amount. However, even in this case, the discharge amount can be corrected into an appropriate amount by adjusting the amount of forward movement of the discharge amount adjustment member 30.

According to the liquid-material discharge device 1 of the first embodiment described above, a discharge amount changed during discharge operation can be corrected by changing the position of the discharge amount adjustment member 30, which leads to easier correction of the discharge amount than conventional techniques. In addition to the discharge amount adjustment member 30 by which the discharge amount is corrected, the discharge amount can be corrected from a plurality of aspects by adjusting the pressure of the pressurized air applied to the liquid-material reservoir 51.

The discharge amount adjustment member 30 allows for reducing an amount of liquid material wasted in cleaning of the liquid feed member 4, while adjusting the amount of liquid material supplied to the liquid chamber 12. Further, since a cross-sectional area of the liquid feed path 13 can be larger than a case of not using discharge amount adjustment member 30, it is possible to shorten time for cleaning of the liquid feed path 13. Furthermore, since the liquid feed path 13 can be larger in diameter than conventional ones, it is easy to perform a visual check after cleaning.

Second Embodiment

A liquid-material discharge device 1 of a second embodiment shown in FIG. 4 is different than the first embodiment mainly in that an extension portion 41 includes a first thread groove 42 formed in an outer periphery at its end and that a discharge amount adjustment member 30 includes a second thread groove 35 formed inside a groove 34. Hereinafter, differences from the first embodiment will be mainly described and descriptions of elements in common will be omitted.

The extension portion 41 of the second embodiment has a small-diameter cylindrical portion 46 at its end, and the first thread groove 42 is formed in the outer periphery of the cylindrical portion 46. The discharge amount adjustment member 30 includes the annular groove 34 formed inside a large-diameter portion 33. The second thread groove 35 is formed in an outer periphery inside the groove 34, and can be fitted with the first thread groove 42 of the extension portion 41 by screwing, resulting in fixing the discharge amount adjustment member 30. The second thread groove 35 of the discharge amount adjustment member 30 and the first thread groove 42 of the extension portion 41 are tightly fitted together by screwing, and the position of the discharge amount adjustment member 30, which has been adjusted by turning the large-diameter portion 33, remains fixed even when the hold on the large-diameter portion 33 is released.

The other configurations are similar to those of the first embodiment and thus descriptions thereof are omitted.

The above-described liquid-material discharge device 1 of the second embodiment also yields similar effects to those in the first embodiment. Further, the thread grooves (35, 42) have no contact with the liquid material, which thus prevents a case where dried liquid material sticks to thread grooves.

Third Embodiment

A discharge amount adjustment member 30 of a third embodiment shown in FIGS. 5 and 6 is different than the first embodiment mainly in that an insertion hole 25 and a plug portion 32 have no thread groove and that the discharge amount is adjusted by sliding the plug portion 32 within the insertion hole 25. Hereinafter, differences from the first embodiment will be mainly described and descriptions of elements in common will be omitted.

The insertion hole 25 of the third embodiment has no thread groove in its inner periphery, and is constituted by a space having a diameter equal to that of a liquid feed path 13. Alternatively, the insertion hole 25 may be provided with a seal member for the discharge amount adjustment member, through which the plug portion 32 is inserted, as in the below-mentioned fourth embodiment.

The plug portion 32 of the discharge amount adjustment member 30 of the third embodiment has no thread groove, and has such a diameter as to slide within the insertion hole 25. The insert portion 31 of the third embodiment is longer than the insert portion 31 of the first embodiment, and has such a length as to reach nearly the liquid chamber 12. Note that the length of the insert portion 31 may be adapted as far as its tip at the forwardmost position in the liquid feed path 13 does not reach the liquid chamber 12. For example, the insert portion 31 of the third embodiment may have the same length as that of the first embodiment.

A configuration of a large-diameter portion 33 is similar to that of the first embodiment. Drawing the large-diameter portion 33 of the insert portion 31 at the position in FIG. 5 in a direction opposite to the liquid chamber 12 allows the discharge amount adjustment member 30 to move backward to the position shown in FIG. 6. The insertion hole 25 and the plug portion 32 are tightly slidably fitted together, and thus the position of the discharge amount adjustment member 30 remains fixed even when the hold on the large-diameter portion 33 is released. The insert portion 31 is moved from the position in FIG. 6 to the position in FIG. 5 by manually pushing the large-diameter portion 33 inward.

When the insert portion 31 is moved from the position in FIG. 5 to the position in FIG. 6, the flow resistance of the liquid material flowing from the reservoir 51 into the liquid chamber 12 decreases and thus the discharge amount increases. Conversely, when the insert portion 31 is moved from the position in FIG. 6 to the position in FIG. 5, the discharge amount decreases.

The other configurations are similar to those of the first embodiment and thus descriptions thereof are omitted.

The above-described discharge amount adjustment member 30 of the third embodiment also yields similar effects to those in the first embodiment.

Fourth Embodiment

A discharge amount adjustment member 30 of a fourth embodiment shown in FIG. 7 is different than the third embodiment mainly in that an insert portion 31 has a ridge 36 and a helical groove 37 in its outer periphery. Hereinafter, differences from the third embodiment will be mainly described and descriptions of elements in common will be omitted.

The insert portion 31 of the fourth embodiment has the ridge 36 and the helical groove 37 formed in its outer periphery. The ridge 36 has a constant width from a start point to an end point thereof, and the helical groove 37 also has a constant width from a start point to an end point thereof. When the insert portion 31 is inserted into a liquid feed path 13, the ridge 36 is in contact with an inner periphery of the liquid feed path 13, and the helical groove 37 serves as a flow path through which the liquid material is supplied to a liquid chamber 12.

An insertion hole 25 and a plug portion 32 of the fourth embodiment have no thread groove, and the discharge amount is adjusted by sliding the plug portion 32 within the insertion hole 25. The insertion hole 25 of the fourth embodiment is constituted by a space having a diameter equal to that of the liquid feed path 13. The insertion hole 25 is provided with a seal member 24 for the discharge amount adjustment member as in the first embodiment.

FIG. 8 is a front sectional view illustrating a discharge amount adjustment method according to the fourth embodiment. (a) shows a state where the discharge amount adjustment member 30 is set at a forwardmost position, and (b) shows a state where the discharge amount adjustment member 30 has been moved backward from the forwardmost position. The insertion hole 25 and the plug portion 32 are tightly slidably fitted together, and thus the position of the discharge amount adjustment member 30 remains fixed even when the hold on a large-diameter portion 33 is released.

In the fourth embodiment, since the ridge 36 is in contact with the inner periphery of the liquid feed path 13, at least the ridge 36 is preferably made of low-hardness material such as rubber or resin to prevent damage to the inner periphery. The discharge amount adjustment member 30 includes, between the plug portion 32 and the large-diameter portion 33, a stepped portion at which an O-ring may be disposed.

The other configurations are similar to those of the first embodiment and thus descriptions thereof are omitted.

The above-described discharge amount adjustment member 30 of the fourth embodiment also yields similar effects to those in the third embodiment. In the fourth embodiment, the ridge 36 serves to scrape out the liquid material, which can reduce the amount of liquid material remaining in the liquid feed path 13 as compared with the third embodiment.

Fifth Embodiment

A discharge amount adjustment member 30 of a fifth embodiment shown in FIG. 9 is different than the fourth embodiment mainly in that an insertion hole 25 and a plug portion 32 each have a thread groove. Hereinafter, differences from the fourth embodiment will be mainly described and descriptions of elements in common will be omitted.

As for an insert portion 31 of the fifth embodiment, the insertion hole 25 has a first thread groove 42 in its inner periphery, and the plug portion 32 has a second thread groove 35 in its outer periphery, as in the first embodiment.

A ridge 36 and a helical groove 37 are similar to those of the fourth embodiment.

FIG. 10 is a front sectional view illustrating a discharge amount adjustment method according to the fifth embodiment. (a) shows a state where the discharge amount adjustment member 30 is set at a forwardmost position, and (b) shows a state where the discharge amount adjustment member 30 has been moved backward from the forwardmost position. The second thread groove 35 of the plug portion 32 and the first thread groove 42 are tightly fitted together by screwing, and the position of the discharge amount adjustment member 30, which has been adjusted by turning a large-diameter portion 33, remains fixed even when the hold on the large-diameter portion 33 is released.

The above-described discharge amount adjustment member 30 of the fifth embodiment also yields similar effects to those in the fourth embodiment.

Sixth Embodiment

A discharge amount adjustment member 30 of a sixth embodiment shown in FIG. 11 is different than the first embodiment mainly in that a forward and backward driving device (a slider 48 and a motor 49) is included to drive the discharge amount adjustment member 30 forward and backward. Hereinafter, differences from the first embodiment will be mainly described and descriptions of elements in common will be omitted.

In the sixth embodiment, an insertion hole 25 has a first thread groove 42 in its inner periphery, and a plug portion 32 has a second thread groove 35 in its outer periphery. The below-mentioned motor 49 is driven to adjust the position of the discharge amount adjustment member 30 and thereby adjust the discharge amount.

A supporting member 47 is disposed under an extension portion 41. The slider 48 is disposed on an upper surface of the supporting member 47, and the motor 49 is slidably mounted on the slider 48. The motor 49 is coupled to a large-diameter portion 33 via a coupling portion 50, and normal and reverse rotation of the motor 49 causes the discharge amount adjustment member 30 to move forward and backward by screwing between the first thread groove 42 and the second thread groove 35. A rotation direction and a rotation number of the motor 49 can be automatically controlled by a controller 64. In the present embodiment, the forward and backward driving device that drives the discharge amount adjustment member 30 forward and backward is configured with the slider 48 and the motor 49. However, the forward and backward driving device is not limited to the illustrated configuration, and may be configured with an electric actuator that slides the plug portion 32 in a forward or backward direction in a configuration without the first thread groove 42 and the second thread groove 35, for example.

The controller 64 adjusts a position of the motor 49 in accordance with instructions input by a user to adjust the discharge amount. For example, when the user inputs an instruction to reduce the discharge amount from an input device (not shown), the motor 49 is moved toward an extension portion 41. When the user inputs an instruction to increase the discharge amount from the input device (not shown), the motor 49 is moved away from the extension portion 41. In the sixth embodiment, it is possible to provide instructions on a movement amount of the discharge amount adjustment member 30 in a quantitative way.

The controller 64 includes a timer program that stores conditions for correcting the discharge amount (that is, a movement amount of the motor 49) in a storage device and executes them at a predetermined timing. If the discharge amount regularly changes over time, the controller 64 may execute the stored correction conditions automatically at regular time intervals. In a case where application is performed for drawing a desired application pattern, an application program that stores a position of the discharge amount adjustment member 30 at each application position and repositions the discharge amount adjustment member 30 during the application for drawing may be incorporated into the controller 64.

According to the above-mentioned discharge device 1 of the sixth embodiment, it is possible to quantitatively control the movement amount of the discharge amount adjustment member 30. It is also possible to correct the discharge amount at a predetermined timing in accordance with the stored conditions for correcting the discharge amount.

The preferred embodiment examples of the present invention have been described above. However, the technical scope of the present invention is not limited to the description of the above-mentioned embodiments. Various alterations and modifications can be applied to the above embodiments, and such altered or modified modes also fall within the technical scope of the present invention. For example, the embodiment examples illustrate a mode where the central axis of the insert portion 31 coincides with the central axis of the discharge amount adjustment member 30. However, the central axis of the insert portion 31 may differ from the central axis of the discharge amount adjustment member 30. In more detail, a configuration where the central axis of the insert portion 31 is positioned below or above the central axis of the discharge amount adjustment member 30 also falls within the technical scope of the present invention.

LIST OF REFERENCE SYMBOLS 1 discharge device/2 upper main body/3 lower main body/4 liquid feed member/5 nozzle fixture/6 nozzle member/7 discharge port/11 discharging member/12 liquid chamber/13 liquid feed path/14 seal member/15 piston chamber/16 piston/17 spring/18 knob/19 stroke adjustment screw/21 seal member/22 seal member/23 through-hole/24 seal member (for discharge amount adjustment member)/25 insertion hole/30 discharge amount adjustment member/31 insert portion/32 plug portion/33 large-diameter portion/34 groove/35 second thread groove/36 ridge/37 helical groove/39 communication groove/40 stirring blade/41 extension portion/42 first thread groove/43 reservoir coupler/44 inlet/45 lateral opening/46 cylindrical portion/47 supporting member/48 slider/49 motor/50 coupling portion/51 reservoir/52 adapter/53 pressure reducing valve/54 air supply source/61 solenoid switching valve/62 pressure regulator/63 air supply source/64 controller/70 cotton swab/81 upper main body/82 middle main body/83 first liquid feed member/84 second liquid feed member/85 lower main body/86 nozzle member/87 liquid chamber/88 liquid feed path/89 plug/91 storage tank/92 pressure reducing valve/93 air supply source

The invention claimed is:

1. A liquid-material discharge device, comprising:
a discharging member having a rod-shaped body;
a liquid chamber wider than the discharging member, in which a tip portion of the discharging member is disposed;
a discharge port communicating with the liquid chamber;
a liquid feed path having an opening provided in the liquid chamber and that makes the liquid chamber communicate with a liquid-material reservoir; and
a driving device configured to drive the discharging member,
wherein the liquid-material discharge device comprises a discharge amount adjustment member positioned at the liquid feed path to adjust resistance in the liquid feed path, and a member position adjustment mechanism configured to shift and fix a position of the discharge amount adjustment member within the liquid feed path,
wherein the member position adjustment mechanism changes the position of the discharge amount adjustment member so that a discharge amount is able to be adjusted.

2. The liquid-material discharge device according to claim 1, wherein the liquid feed path includes a linear flow path having an end opening, and the discharge amount adjustment member is constituted by an elongated member inserted in the liquid feed path.

3. The liquid-material discharge device according to claim 1, comprising a seal member through which the discharge amount adjustment member is inserted.

4. The liquid-material discharge device according to claim 1, wherein the discharge amount adjustment member has a length of one-half to one times a length L of the liquid feed path.

5. The liquid-material discharge device according to claim 1, wherein a tip portion of the discharge amount adjustment member is positioned at a liquid-chamber side from an inlet via which the liquid-material reservoir is connected to the liquid feed path.

6. The liquid-material discharge device according to claim 1, wherein the member position adjustment mechanism is constituted by a first thread groove formed on a liquid feed member in which the liquid feed path is formed, and a second thread groove formed on the discharge amount adjustment member corresponding to the first thread groove.

7. The liquid-material discharge device according to claim 1, wherein the member position adjustment mechanism is constituted by a forward and backward driving device configured to drive the discharge amount adjustment member forward and backward.

8. The liquid-material discharge device according to claim 7, wherein a volume of the liquid feed path is adjusted by driving the discharge amount adjustment member forward and backward.

9. The liquid-material discharge device according to claim 7, comprising a control device configured to control positioning of the discharge amount adjustment member by the forward and backward driving device at a preset timing.

10. The liquid-material discharge device according to claim 1, wherein the discharge amount adjustment member is removably inserted into the liquid feed path.

11. The liquid-material discharge device according to claim 1, wherein the discharge amount adjustment member has a recessed and projected portion formed on a longitudinal surface.

12. The liquid-material discharge device according to claim 11, wherein the recessed and projected portion is constituted by a ridge in contact with an inner periphery of the liquid feed path and a groove positioned between sections of the ridge.

13. The liquid-material discharge device according to claim 12, wherein the groove positioned between sections of the ridge is a helical groove.

14. The liquid-material discharge device according to claim 1, wherein the discharge amount adjustment member is selected out of a plurality of discharge amount adjustment members different in one or more of a cross-sectional area, a cross-sectional shape, and a length, and the selected discharge amount adjustment member is able to be removably inserted into the liquid feed path.

15. The liquid-material discharge device according to claim 1, wherein the discharging member is constituted by a plunger of which tip portion moves forward and backward within the liquid chamber, or a screw of which tip portion rotates within the liquid chamber.

16. The liquid-material discharge device according to claim 1, wherein the discharging member is a plunger extending vertically, the driving device is configured to move the discharging member forward and backward, and the plunger is moved forward to collide against a valve seat provided on an inner bottom surface of the liquid chamber, or is moved forward and stopped immediately before colliding against the valve seat, so that a liquid droplet is discharged and flown from the discharge port.

17. The liquid-material discharge device according to claim 1, wherein the discharge amount adjustment member is kept from interrupting communication between the liquid chamber and the liquid-material reservoir even when moved by the member position adjustment mechanism.

18. The liquid-material discharge device according to claim 1, wherein the member position adjustment mechanism is able to lower flow resistance in the liquid feed path by moving the discharge amount adjustment member backward from a forwardmost position.

19. A liquid-material discharge method using the liquid-material discharge device according to claim 1, the method comprising:

adjusting the resistance in the liquid feed path by the discharge amount adjustment member; and shifting and fixing the position of the discharge amount adjustment member within the liquid feed path.

20. The liquid-material discharge device according to claim 1, wherein the liquid feed path includes an end opening formed on the opposite side of the opening, and the discharge amount adjustment member is constituted by an elongated member inserted in the liquid feed path through the end opening.

* * * * *